United States Patent [19]

Emmert et al.

[11] Patent Number: 5,009,711

[45] Date of Patent: Apr. 23, 1991

[54] GOLDEN COLOR LUSTER PIGMENTS

[75] Inventors: Ralf Emmert, Bayonne, N.J.; Manfred Weigand, Darmstadt, Fed. Rep. of Germany

[73] Assignee: Merck Patent Gesellschaft mit Beschrankter Haftung, Darmstadt, Fed. Rep. of Germany

[21] Appl. No.: 243,540

[22] Filed: Sep. 12, 1988

[30] Foreign Application Priority Data

Sep. 11, 1987 [DE] Fed. Rep. of Germany ....... 3730505

[51] Int. Cl.[5] ............................................. C04B 14/20
[52] U.S. Cl. .................... 106/415; 106/417; 106/439; 424/64
[58] Field of Search ............... 106/415, 417, 439, 459; 424/64, 69

[56] References Cited

U.S. PATENT DOCUMENTS

| | | | |
|---|---|---|---|
| 3,087,828 | 4/1963 | Linton | 106/417 |
| 3,711,308 | 1/1973 | Brand et al. | 106/417 |
| 3,874,890 | 4/1975 | Bernhard et al. | 106/418 |
| 3,926,659 | 12/1975 | Bernhard et al. | 106/418 |
| 4,036,662 | 7/1977 | Rademachers et al. | 106/439 |
| 4,084,984 | 4/1978 | Hund et al. | 106/439 |
| 4,086,100 | 4/1978 | Esselborn et al. | 106/417 |
| 4,146,403 | 3/1979 | Armanini et al. | 106/418 |
| 4,744,832 | 5/1988 | Franz et al. | 106/418 |
| 4,867,794 | 9/1989 | Ambrosius et al. | 106/415 |

FOREIGN PATENT DOCUMENTS

| | | | |
|---|---|---|---|
| 1201255 | 3/1986 | Canada | 106/439 |
| 99975 | 7/1980 | Japan | 106/417 |

OTHER PUBLICATIONS

"Concise Chemical and Technical Dictionary", Bennett, H., ed., Chemical Publishing, Co., Inc., 1974, p. 867.

Primary Examiner—Melvyn J. Andrews
Assistant Examiner—George Wyszonierski
Attorney, Agent, or Firm—Millen, White & Zelano

[57] ABSTRACT

The application relates to a preferably golden color luster pigment based on lamellar substrates, in particular mica, which have been coated with metal oxides, the metal oxide layer containing both titanium and iron and the pigment containing mainly a pseudobrookite layer formed by simultaneous precipitation of the metal oxides. This golden color luster pigment is suitable for cosmetic articles because of its physiological acceptability and is particularly suitable for silicate melts because of its resistance to heat and chemicals.

20 Claims, No Drawings

GOLDEN COLOR LUSTER PIGMENTS

BACKGROUND OF THE INVENTION

The invention relates to color luster pigments based on lamellar substrates coated with a metal oxide layer, in particular mica or mica coated with metal oxides, the metal oxide layer containing both titanium and iron.

Mica flake pigments containing iron are known and have also been used successfully for many years. This term describes both pigments in which iron oxide is precipitated, together with another metal oxide, in particular titanium dioxide, onto the mica platelet, and pigments in which the precipitations are carried out successively.

It is described in U.S. Pat. No. 3,087,828 that golden pigments which assume a reddish color shade on being calcined are obtained by depositing an $Fe_2O_3$ layer onto a $TiO_2$ layer. Pigments which contain, on mica, first a mixed layer of titanium oxide and iron oxide and above that a top layer of titanium dioxide and/or zirconium dioxide are described in German Patent No. 1,959,998.

German Patent No. 2,244,298 describes a process for the preparation of golden pearly luster pigments in which a mica pigment coated with $TiO_2$ and/or $ZrO_2$ is first coated with iron(II) hydroxide, and the latter is then oxidized to $Fe_2O_3$.

Finally, mica pigments which carry a thick layer of $Fe_2O_3$ on a very thin layer of $TiO_2$ or $Al_2O_3$ are described in German Offenlegungsschrift No. 2,723,871.

It has also already been suggested in German Patent No. 2,522,572 to provide mica pigments which have been coated with $TiO_2$ in rutile form with an additional top layer composed of coloring metal oxides, $Fe_2O_3$ also being mentioned. In fact, coatings of this type have also been carried out using relatively small amounts of iron oxide.

Advantageous pigments containing iron, in which the iron oxide is present in specific defined crystal modifications, are described in German Offenlegungsschrift No. 2,313,331.

In the process of German Offenlegungsschrift No. 3,528,256, mica pigments coated with titanium dioxide in rutile form are coated with a relatively large amount of iron oxide, so that a three-layer structure of rutile, pseudobrookite and iron oxide is formed, as can be demonstrated by X-ray structural analysis.

The golden color luster pigments based on mica coated with metal oxide hitherto known have an inadequate resistance to chemicals and heat in vitreous enamels and glazes or are unsuitable for use in cosmetics owing to the addition of toxic heavy metals.

SUMMARY OF THE INVENTION

It is therefore an object of the invention to provide new color luster pigments and a new process for their preparation. It is a further object to provide pigments having a high stability to chemicals and heat in order to enable them to be used in silicate melts, and, in addition, having no toxic constituents to permit their use in cosmetic articles.

Upon further study of the specification and appended claims, further objects and advantages of this invention will become apparent to those skilled in the art.

These objects have been satisfied by the provision of very stable pigments having a mixed oxide layer which has been precipitated under suitable conditions onto lamellar substrates and which consists mainly of pseudobrookite. Their high stability to heat and chemicals makes it possible for them to be employed in glazes and vitreous enamels.

The invention therefore relates to color luster pigments based on lamellar substrates coated with a metal oxide layer, in particular mica or mica coated with metal oxides, the metal oxide layer containing both titanium and iron, characterized in that the metal oxide layer contains essentially pseudobrookite.

The invention also relates to a process for the preparation of color luster pigments by coating lamellar substrates, such as glass, mica or mica coated with metal oxides, with a metal oxide layer containing iron and titanium and subsequent calcination, which is characterized in that an aqueous iron(III) salt solution, an aqueous titanium(IV) salt solution and a base are simultaneously added to an aqueous suspension of a lamellar substrate at a temperature between 50° and 100° C., a pH between 2.0 and 6.0 in such a way that a molar ratio of iron to titanium such as 1.5–2.5:1 is maintained and the pH remains virtually constant during the whole coating operation.

The invention also relates to the use of these color luster pigments in plastics, paints, cosmetics and silicate melts, such as vitreous enamels and glazes.

DETAILED DISCUSSION

Surprisingly, pigments having a homogeneous layer of this type composed of pseudobrookite have both markedly improved coloristic properties (improved tinctorial strength and brilliance and improved hiding power) and an improved resistance to chemicals, particularly in relation to stability in melts for glazes and vitreous enamels, and also an improved photoactivity. This manifests itself in high luster and great color fidelity after firing. Whereas the hitherto known golden color luster pigments faded and their color became dull and turned brown-yellow when fired in vitreous enamels or glazes, the vitreous enamels and glazes obtained by means of the new golden color luster pigments are more lustrous and more similar in color to real gold.

The good properties of this pseudobrookite layer manifest themselves over the whole range of the composition $(Fe_2O_3)_x \cdot (TiO_2)$ in which x can assume any value between 0.75 and 1.5. The composition in which $x=1$, which corresponds to the exact stoichiometric composition of pseudobrookite, $Fe_2TiO_5$, is, however, particularly preferred.

It is essential that the new color luster pigments should have a very smooth surface corresponding to the smooth surface to be coated of the substrates employed. For this reason, these color luster pigments can only be prepared if definite process conditions are observed. The hydrolysis should therefore be carried out at, as far as possible constant temperature, constant pH and constant inflow rate of the metal salt solution. It is essential in this regard that an excess of metal ions in the suspension should be avoided. Thus only the amount of metal salt that can be absorbed per time unit in the form of hydrated metal oxide by the substrate surface may be supplied to the hydrolysis per unit time. Homogeneous layers of uniform layer thickness are only obtained if steps are taken to prevent the presence in the suspension of free, hydrated metal ions or metal oxide particles which are not attached to the substrate surface.

In principle, any lamellar materials which can be coated with metal oxides are suitable for use as substrates for the precipitation of the metal oxide layer. Examples which can be mentioned are glass or micas, such as, for example, muscovite, biotite, phlogopite and vermiculite, synthetic micas and mica coated with metal oxides.

It is preferable to employ muscovite, clear grades of mica having a low content of coloring metal compounds being preferred. In special cases, however, colored grades of mica are also suitable for achieving a specific color character.

Particularly advantageous pigments are also obtained when using mica previously coated with, preferably, 1-5% by weight of $SiO_2$, $SnO_2$, $Al_2O_3$, $TiO_2$ and/or $Fe_2O_3$.

Depending on the desired subsequent use of the color gloss pigment, the mica flakes preferably used have a diameter of about 2-1,000 $\mu$m, preferably 5-50 $\mu$m, and a thickness in the range of about 0.05-1 $\mu$m, preferably about 0.1 $\mu$m. Mica is not suitable for the color gloss pigments according to the present invention if its thickness exceeds 1 $\mu$m. The mica flakes should be as uniform as possible in respect of thickness and diameter. It is therefore preferable to classify the mica after it has been split and ground. By "diameter" is meant the longer dimension of the lamellar flake.

The substrate to be coated is initially taken in aqueous suspension, preferably in a concentration of about 5-40% by weight. The metal salt solutions are introduced uniformly into the suspension at one or more points. If appropriate, it is also possible to premix the metal salt solutions in the desired ratio before they are added to the substrate suspension. The iron salt solution is preferably employed in a concentration of about 0.1-4 mol/liter and the titanium salt solution in a concentration of about 0.05-2 mol/liter. The molar ratio of iron to titanium in the metal salt solutions is generally about 1.5 to 2.5:1, preferably 1.8 to 2.2:1 and especially 2.0:1. Metal oxide layers having an iron content, calculated as $Fe_2O_3$, of 60-72% by weight, preferably about 53-69% by weight and particularly 67% by weight, are obtained in this way.

In principle, any water-soluble salts of the metals mentioned can be employed as metal salts. It is preferable to use the chlorides. Compared with the sulfates, which in other respects are also readily accessible, the chlorides have the advantage that the chloride ion is not so firmly attached in the hydrated metal oxide as the sulphate ion. It can therefore be washed out again more easily.

The metal oxides are precipitated on the substrate surface without secondary precipitation taking place. This is preferably achieved by regulating the inflow rate in such a way that about $0.01-25 \times 10^{-5}$ mol of metal ions per minute and per square meter are supplied to the surface to be coated.

A base, preferably an aqueous, 0.025-10 molar solution of alkali metal hydroxide or ammonium hydroxide or an equivalent amount of gaseous ammonia, is introduced at the same time as the metal salt solution(s). Suitable alkali metal hydroxides are essentially sodium hydroxide and potassium hydroxide. The addition of the base is controlled so that, essentially, the pH which has been selected at the start of the coating, within the range from about 2 to 65, is always maintained.

In order to keep the pH constant, it is also possible to add buffer systems, for example phosphate, acetate, citrate and glycocoll buffers. These can either be initially placed in the suspension of mica flakes or, more advantageously, added with the solution of alkali metal hydroxide or ammonium hydroxide. In many cases, however, the addition of further extraneous ions is not desirable, so that it is preferable to maintain the desired pH at a constant level by metering in the base accurately.

The coating time can be varied considerably. It depends essentially on the concentration of the metal salt solution fed in, the surface of the substrate to be coated and the thickness of the layer of pseudobrookite to be applied. As a rule, times of about 1-24 hours are used.

The color luster pigment obtained by the process according to the invention can be worked up and isolated from the reaction mixture by any customary method. It is advantageous to subject it to heat treatment at about 50°-100° C. in the suspension, with stirring, for a further ½-4 hours, the result of which is to compact the oxide layer. The pigment is then preferably washed, if appropriate after the pH has been adjusted to 5-7. Drying is carried out in a manner customary per se at temperatures of about 90° to 150° C.

Depending on the color shade desired, the total layer thickness of the precipitated layers preferably varies between about 30 and about 180 nm. As is known, as the layer thickness increases the interference color changes continuously from blue-gray via silver, gold, orange, red, violet and blue to green. Subsequently, interference colors of a higher order are obtained. Layer thicknesses within the range between 30 and 180 nm are preferred, since they correspond to interference colors of the first order. The interference color gold is particularly preferred.

The resulting pigments are sensitive to light and are therefore preferably stabilized in a manner known per se by calcination at temperatures of 700°-1,100° C., preferably 900°-1,000° C. They thereby also become resistant to the effects of temperature.

After drying and calcination, in which the metal oxide layer is substantially dehydrated, pigments are obtained which have a content of 10 to 60%, preferably 20 to 50%, of the pseudobrookite layer, relative to the total weight of pigment.

Doping substances, in particular other colored or colorless metal oxides, can also be incorporated in the pseudobrookite layer. Suitable examples of these are compounds of aluminum(III), silicon(IV), tin(IV), zirconium(IV), chromium(III), boron(III) and phosphorus(V). These doping substances are introduced, if appropriate, in amounts of 0-2% by weight in each case. Overall, however, the amount should not exceed 2-5% by weight.

If doping substances are to be incorporated in the layer, these substances can be added in the form of water-soluble salts to the suspension of mica, to one of the salt solutions added or, if appropriate, also to the base metered in. As a rule, the doping substances are homogeneously distributed in the metal oxide layer. However, it is also possible, and in some cases advantageous, to effect an enrichment either in the vicinity of the mica or at the surface of the pigment.

It is also possible to subject the pigments to an after-coating or after-treatment which further increases the stability to light, weathering and chemicals or facilitates the handling of the pigment, particularly its incorporation into various media. Examples of suitable after-coating or after-treatment are the processes described in German Patent No. 2,215,191 or German Offenlegungsschriften Nos. 3,151,354, 3,235,017 or 3,334,598.

Because the properties of the pigments according to the invention are already very good without these additional measures, these optionally applied substances amount to only about 0–5%, in particular 0–3% by weight of the total pigment.

Particularly advantageous pearl luster pigments which are far superior to those hitherto known in color and luster when used in silicate melts are obtained in accordance with the present invention. Thus it is possible to obtain an advantageous gold pigment by means of which, after incorporation into, for example, glazes and/or vitreous enamels, articles are obtained approximating, in color, luster and beauty, to articles which have been colored by means of metallic gold.

The frits used are silicate melts having a composition and properties known from the literature (for example Winnacker-Kuchler, Chemische Technologie ("Chemical Technology") volume 2, Anorg. Technologie ("Inorganic Techonlogy II"), Carl-Hanse-Verlag, Munich, 1959), preferably frits having a melting range between 500° and 1,100° C.

Besides the possible applications which are normally customary, the new pigments are also particularly suitable for cosmetic purposes, since they are composed of physiologically acceptable metal oxides. In the main, however, they are employed as pigments for coloring, for example, plastics, cosmetic articles such as lipsticks and soap, glass, ceramics, paints and rubber and rubber goods. Because of their heat resistance they are also suitable, above all, for stoving paints and for coloring melts, glass and ceramic material which is fired. As a rule, the pigments ar employed in amounts of up to 30%, preferably about 0.5–10%. In plastics, the proportion is relatively low, as a rule, for example, lipsticks, up to 30%, preferably 5–25%, relative to the total weight of lipstick, can be used.

When incorporated, for example, into plastic films, the new pigments display strong colors which do not change even if the angle of observation is altered, since these colors are not only inference colors but are also perceived colors. Thus, for example, a plastic film containing a golden pigment according to the present invention displays a strong, beautiful golden color, whereas a corresponding pigment without coloring metal oxide displays a less deeply colored golden-yellow interference color when seen by reflected light and the pale blue complementary color when seen by transmitted light. The pigments according to the invention, on the other hand, also have the yellow intrinsic color of iron/titanium oxide when seen by transmitted light.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

650 ml of an aqueous solution of $FeCl_3$ (152 g of $FeCl_3$/liter), at a metering rate of 1 ml per minute, and 650 ml of an aqueous solution of $TiCl_4$ (90 g of $TiCl_4$/liter), at a metering rate of 1.0 ml per minute, are added simultaneously, at a temperature of 75° C. and a pH of 4.0, to a suspension of 100 g of muscovite having a particle diameter of about 10–100 μm in 2,000 ml of demineralized water. After approx. 1 hour, the metering rates of both solutions are doubled. During the whole time of addition the pH is kept constant by simultaneous dropwise addition of 10% sodium hydroxide solution. After stirring for a further ½ hour, the pigment is separated off, washed with water, dried at 120° C. and calcined at 900° C. for 30 minutes.

This gives a golden, lustrous pigment of high hiding power, whose color and luster are retained in glazes and vitreous enamels even after firing at temperatures between 500° and 1,100° C.

Analysis indicates a Fe:Ti molar ratio of 2:1, and the X-ray structural analysis indicates a pseudobrookite lattice type ($Fe_2TiO_5$).

Example 2

100 g of muscovite coated with $SiO_2$ (2% by weight) by a known process and having a particle diameter of 10–100 μm are suspended in 2,000 ml of demineralized water. 1,300 ml of an aqueous solution containing 99 g of $FeCl_3$ and 58 g of $TiCl_4$ are metered in at a rate of 2 ml per minute at 75° C. and a pH of 4.0, the pH being kept constant by simultaneous dropwise addition of 10% sodium hydroxide solution. After being stirred for a further ½ hour, the pigment is separated off, washed with water, dried at 120° C. and calcined at 900° C. for 30 minutes.

This gives a golden, lustrous pigment of high hiding power, whose color and luster are retained in glazes and vitreous enamels even after firing at temperatures between 500° and 1,100° C.

Analysis indicates an Fe:Ti molar ratio of 2:1, and X-ray structural analysis indicates a pseudobrookite lattice type ($Fe_2TiO_5$).

Example 3

100 g of muscovite are treated analogously to Example 1 with 500 ml of an aqueous solution of $FeCl_3$ (152 g of $FeCl_3$/liter) and 540 ml of an aqueous solution of $TiCl_4$ (90 g of $TiCl_4$/liter).

This gives a golden, lustrous pigment which is hardly inferior in hiding power and heat stability to that from Example 1.

Analyses indicate a Fe:Ti molar ratio of 1.5:1.

Example 4

100 g of muscovite are treated analogously to Example 2 with 1,450 ml of an aqueous solution containing 122 g of $FeCl_3$ and 58 g of $TiCl_4$.

This gives a golden, lustrous pigment which is hardly inferior in hiding power and heat stability to that from Example 1.

Analyses indicate an Fe:Ti molar ratio of 2.5:1, together with a distorted pseudobrookite lattice type.

Example 5

100 g of a muscovite coated with $Al_2O_3$ (2% by weight) by a known process are treated analogously to Example 2.

This gives a golden, lustrous pigment of high hiding power, whose color and luster are retained in glazes and vitreous enamels even after firing at temperatures between 500° and 1,100° C.

Example 6

100 g of a muscovite coated with $SnO_2$ (2% by weight) by known processes are treated analogously to Example 1.

This gives a golden, lustrous pigment of high hiding power, whose color and luster are retained in glazes and vitreous enamels even after stoving at temperatures between 500° and 1,100° C.

Example 7

15 g of the color luster pigment prepared in accordance with Example 1 are mixed with 100 g of a vitreous enamel slip consisting of 60% by weight of the commercially available frit TR 2524 (Bayer, Leverkusen), 3.5% by weight of blue shade, 0.2% by weight of sodium aluminate, 0.2% by weight of potassium carbonate and 36.1% by weight of water. 115 ml of a 2% acrylate solution (Rohagit SD 15 made by Roehm, Darmstadt) are added to this mixture and the pH is adjusted to 10 by means of a 25% ammonia solution. The mixture thus obtained is sprayed onto a steel sheet which has already been primed with vitreous enamel, and is dried and fired at 820° C. for 3–4 minutes.

This gives a lustrous, golden vitreous enamel with a smooth surface.

Example 8

2.0 g of the color luster pigment prepared in accordance with Example 1 are mixed with 3.0 g of the commercially available frit M 204 (Nitto Shokai) and the mixture is made into a paste with 8.8 g of a screen printing oil. This mixture is applied to previously glazed body by the screen printing process and is fired at 730° C. for 30 minutes.

This gives a lustrous, golden layer of glaze with a smooth surface.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A lustrous, colored pigment, comprising a lamellar substrate coated with a topmost metal oxide layer containing both titanium and iron wherein said metal oxide layer consists essentially of pseudobrookite.

2. A pigment according to claim 1, wherein the metal oxide layer has the composition $(Fe_2O_3)_x(TiO_2)$, wherein X is 0.75–1.5.

3. A pigment according to claim 2, wherein x is 1.

4. A pigment according to claim 1, wherein the substrate is glass, mica, synthetic mica or mica coated with at least one metal oxide.

5. A pigment according to claim 1, wherein the substrate is mica coated with at least one metal oxide.

6. A pigment according to claim 5, wherein the mica is muscovite, biotite, phlogopite or vermiculite.

7. A pigment according to claim 6, wherein the mica is muscovite.

8. A pigment according to claim 5, wherein the substrate is mica coated with at least one of $SiO_2$, $SnO_2$, $Al_2O_3$, $TiO_2$ or $Fe_2O_3$.

9. A pigment according to claim 5, wherein the mica has a diameter of about 2–1000 $\mu$m and a thickness of 0.05–1 $\mu$m.

10. A pigment according to claim 1, wherein the metal oxide layer has an iron content, calculated as $Fe_2O_3$, of 60–72% by weight.

11. A pigment according to claim 1, wherein the pseudobrookite content is 10–60% based on the total weight of the pigment.

12. A pigment according to claim 1, further comprising up to 5% of Al(III), Si(IV), Sn(IV), Zr(IV), Cr(IV), B(III) or P(V).

13. In a vitreous enamel or glaze containing a lustrous colored pigment, the improvement wherein the pigment is that of claim 1.

14. In a cosmetic preparation containing a lustrous colored pigment, the improvement wherein the pigment is that of claim 1.

15. A process for the preparation of a lustrous colored pigment, comprising simultaneously adding to an aqueous suspension of a lamellar substrate an aqueous salt solution or solutions containing Fe(III), Ti(IV) and a base so that a topmost layer consisting essentially of pseudobrookite is produced on the substrate.

16. A process according to claim 15, wherein during said adding step the temperature is about 50°–100° C., the pH is about 2.0–6.0, and the molar ratio of Fe to Ti is about 1.5–2.5:1.

17. A process according to claim 15, wherein the metal salts are supplied at a rate so that about the amount of metal salt that can be absorbed as hydrated metal oxide on the substrate surface is supplied per unit of time.

18. A process according to claim 17, wherein an iron salt is employed in a concentration of 0.1–4 mol/l, an titanium salt is employed in a concentration of 0.05–2 mol/l, the molar ratio of iron to titanium is about 1.5–2.5:1, and the inflow rate of the aqueous solution or solutions is regulated so that $0.01-25 \times 10^{-5}$ mol of metal ions per minute and per square meter are supplied to the substrate.

19. A pigment prepared by the process of claim 15.

20. A pigment prepared by the process of claim 18.

* * * * *